United States Patent [19]

Baigrie et al.

[11] 4,248,956

[45] * Feb. 3, 1981

[54] PHOTOGRAPHIC PRODUCTS AND PROCESSES EMPLOYING HETEROCYCLIC AZO DYE DEVELOPER COMPOUNDS

[75] Inventors: Brian D. Baigrie, New Denham; Joseph Bailey, Harrow; Linda G. Johnston, Harrow; Miroslav V. Mijovic, Harrow, all of England

[73] Assignee: Eastman Kodak Company, Rochester, N.Y.

[*] Notice: The portion of the term of this patent subsequent to Mar. 6, 1996, has been disclaimed.

[21] Appl. No.: 16,998

[22] Filed: Mar. 2, 1979

Related U.S. Application Data

[63] Continuation-in-part of Ser. No. 822,188, Aug. 5, 1977, Pat. No. 4,142,891.

[51] Int. Cl.³ .............. G03C 1/40; G03C 5/54; G03C 1/10; G03C 7/00
[52] U.S. Cl. ................... 430/225; 430/237; 430/243; 430/562
[58] Field of Search ............. 96/29 D, 77, 99, 73; 430/225, 243, 562, 237

[56] References Cited

U.S. PATENT DOCUMENTS

| | | | |
|---|---|---|---|
| 3,453,107 | 7/1969 | Idelson | 96/29 D |
| 3,563,739 | 2/1971 | Idelson | 96/29 D |
| 3,932,380 | 1/1976 | Krutak et al. | 96/29 D |
| 4,099,972 | 7/1978 | Sato et al. | 96/77 |
| 4,142,891 | 3/1979 | Baigrie et al. | 96/77 |
| 4,147,544 | 4/1979 | Anderson et al. | 96/77 |
| 4,148,641 | 4/1979 | Green et al. | 96/77 |
| 4,148,642 | 4/1979 | Chapman et al. | 96/77 |

*Primary Examiner*—Richard L. Schilling
*Attorney, Agent, or Firm*—Harold E. Cole

[57] ABSTRACT

Photographic elements, diffusion transfer assemblages and processes are described which employ a novel dye developer compound having a dye moiety such as an arylazo-pyrazolotriazole. The compound contains:
 (a) a nitrogen atom in a metal chelating location in at least one of the rings attached to the azo group;
 (b) in the ortho position of the arylazo moiety a metal chelating group (or a salt thereof or a hydrolyzable precursor thereof), and
 (c) a silver halide developer moiety.

The dye developer is transferred imagewise to an image-receiving layer where it is contacted with metal ions to form a metal-complexed dye developer transfer image of excellent stability.

26 Claims, No Drawings

PHOTOGRAPHIC PRODUCTS AND PROCESSES EMPLOYING HETEROCYCLIC AZO DYE DEVELOPER COMPOUNDS

This application is a continuation-in-part of our copending application Ser. No. 822,188, filed Aug. 5, 1977, now U.S. Pat. No. 4,142,891, issued Mar. 6, 1979.

This invention relates to photography and more particularly to color diffusion transfer photography employing certain dye developer compounds which, as a function of development of a silver halide emulsion layer, form an imagewise distribution of unoxidized dye developer. Highly stable metal complexes of this dye are formed in an image-receiving layer.

Diffusion transfer color processes have been described in a number of patents, including U.S. Pat. No. 2,983,606, wherein photographic elements containing silver halide emulsion layers and layers containing diffusible dye developers (dyes having a silver halide developing function) are exposed to record the latent image in the silver halide, and then treated with an alkaline processing composition which permeates the emulsion layers and layers containing the dye developers which then develop the latent images to silver images. At the same time, oxidation products of the dye developers are formed in situ with the silver images and which are relatively nondiffusing in the colloid vehicle of the layers.

The nondiffusing character of the oxidized dye developers is apparently due, at least in part, to a decrease in solubility in the alkaline processing liquid, and may also be due to a hardening effect of the oxidized developer upon the colloid vehicles of the layers which retards the diffusion of the oxidized dye developers. The residual unoxidized dye developers remaining in the layers in imagewise distribution are transferred by diffusion to a superposed reception element substantially to the exclusion of the silver image and oxidized dye developer to provide a positive dye image.

When an element containing differently sensitized silver halide emulsion layers is used and substructively colored dye developers are present in or contiguous to the respective emulsion layers, the dye developers are oxidized and rendered nondiffusing in the developed regions of the layers upon treatment with the processing liquid. The residual dye developer images in the positive regions are transferred by diffusion and in register to the reception element to provide a multicolor reproduction.

Azo dye developers containing metallizable groups are disclosed in U.S. Pat. Nos. 3,081,167; 3,086,005; 3,196,014; 3,299,041; 3,453,107; and 3,563,739. U.S. Patents 3,086,005; 3,492,287 and 3,985,499 disclose various azo dyes, U.S. Pat. Nos. 2,348,417; 2,495,244; and 2,830,042 and French Pat. Nos. 1,124,882 and 1,200,358 disclose various dyes from azopyridines, while U.S. Pat. Nos. 2,868,775; 2,938,895; 3,097,196; 3,691,161; and 3,875,139; British Pat. No. 899,758; and an article entitled "The Irgalan Dyes—Neutral-Dyeing Metal-Complex Dyes" by Guido Schetty, J. Soc. Dyers and Colourists, Volume 71, 1955, pages 705 through 724, disclose various metal complexed dyes. However, neither the specific compounds employed in the instant invention nor the results obtained therewith are disclosed.

It would be desirable to provide improved dye developer compounds containing chelating dye moieties, so that metal-complexed, dye transfer images can be formed having better hues than those of the prior art, as well as good stability to heat, light and chemical reagents.

A photographic element in accordance with our invention comprises a support having thereon at least one photosensitive silver halide emulsion layer having associated therewith a dye developer compound having the following formula:

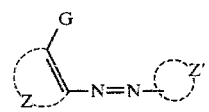

wherein:

Z represents the atoms necessary to complete an aromatic carbocyclic or heterocyclic nucleus having at least one ring of 5 to 7 atoms, such as phenyl, pyridyl, naphthyl, pyrazolyl, indolyl, etc;

Z' is an aromatic carbocyclic or heterocyclic nucleus having at least one ring of 5 to 7 atoms (e.g., the same nuclei as described above for Z), the Z' having, in a position adjacent to the point of attachment to the azo linkage, either (a) a nitrogen atom in the ring of the nucleus which acts as a chelating site, or (b) a carbon atom in the ring of the nucleus having directly attached thereto a nitrogen atom which acts as a chelating site;

G is a metal chelating group (any group which will donate a pair of electrons to a metal ion) or a salt thereof (e.g., an alkali metal salt, a quaternary ammonium salt, etc) or a hydrolyzable precursor thereof (e.g., a hydrolyzable acyl or ester group), e.g., hydroxy; amino; caboxy; sulfonamido; sulfamoyl; a hydrolyzable ester group having the formula $-OCOR^1$, $-OCOOR^1$, $-OCON(R^1)_2$ or $-COOR^1$, wherein $R^1$ is an alkyl group having 1 to about 4 carbon atoms, such as methyl, ethyl, isopropyl, butyl and the like, or an aryl group having 6 to about 8 carbon atoms, such as phenyl, etc; the compound containing a silver halide developing moiety.

In the above formula, G can be either a monovalent group or a nitrogen atom as part of a heterocyclic ring fused to Z. In this later instance, the Z and G atoms can form a nucleus which is the same as the Z' nucleus.

We have found that the use of a nitrogen atom as a chelating site in or adjacent to the ring as described above is generally important in providing metallized dye complexes with narrow spectral absorption bands, much less unwanted absorption, and very good hues. This specific nitrogen atom chelating site is to be contrasted with oxygen atom chelating sites of the hydroxyl and/or carboxyl radicals substituted on aryl nuclei at positions ortho and ortho-prime to the azo linkage, such as described in the above-mentioned U.S. Pat. No. 3,196,014, which generally give rather broad spectra with unwanted absorption.

Z' may be selected from a wide variety of aromatic carbocyclic or heterocyclic nuclei having at least one ring of 5 to 7 atoms and a nitrogen atom in the specific location described above, and include, for example:

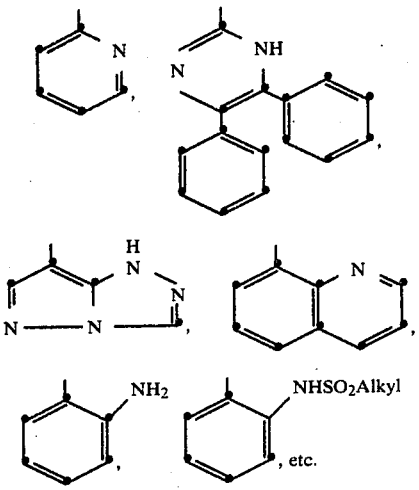

wherein "Alkyl" has from 1 to 6 carbon atoms.

In a preferred embodiment of our invention, Z represents the atoms necessary to complete an aryl group such as a phenyl group and Z' represents a pyrazolotriazole nucleus. These compounds may be described as having a 7-arylazo-pyrazolotriazole dye moiety containing:

(a) in the ortho position of the arylazo moiety a metal chelating group, a salt thereof or a hydrolyzable precursor thereof, and (b) a silver halide developing moiety. Any silver halide developing moiety can be employed in the dye developers of our invention, as long as it is capable of developing an exposed silver halide emulsion under photographic processing conditions. In a preferred embodiment, the silver halide developer moiety is either a benzene or naphthalene radical which is substituted by at least two groups selected from the group consisting of hydroxyl and amino groups which are situated ortho or para to each other so as to be capable of developing an exposed silver halide emulsion.

In a preferred embodiment of the invention, the 7-arylazo-pyrazolotriazole dye developer compound may be represented by the formula:

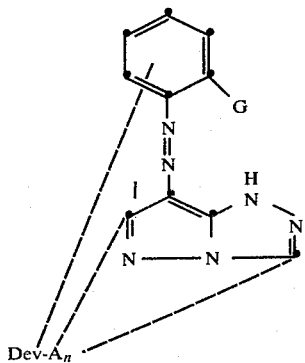

wherein:
G is a metal chelating group, a salt thereof or a hydrolyzable precursor thereof, as defined above;

A is an organic divalent linking radical;
n is either 0 or 1; and
Dev is a dihydroxyphenyl substituent.

In the above formula, A can be any divalent linking radical, such as:

described in U.S. Pat. No. 3,288,778; aminophenalkylthio substituents such as disclosed in U.S. Pat. No. 3,009,958; aminoalkylamino substitutents such as disclosed in U.S. Pat. No. 3,002,997; alkylthio substituents such as disclosed in U.S. Pat. No. 3,043,690; aminoalkyl substituents such as described in U.S. Pat. No. 3,062,884; amnophenyl substituents such as disclosed in U.S. Pat. No. 3,134,811; the acyl substituents disclosed in U.S. Pat. No. 3,142,564; the aminophenoxy substituents such as disclosed in U.S. Pat. No. 3,061,434; lower alkylene and the various other linking substituents disclosed in U.S. Pat. No. 3,255,001, etc. Where the linking substituent is alkylene or contains an alkyl or alkylene moiety, the number of carbon atoms is preferably 1 to 4.

Examples of dihydroxyphenyl substituents useful in the above formula include ortho-dihydroxyphenyl, paradihydroxyphenyl and nuclear-substituted derivatives thereof, e.g., chloro, methyl, phenyl, and/or methoxy-substituted derivatives thereof, particularly nuclear-substituted p-dihydroxyphenyls such as methylhydroquinonyl, p-methyl-phenylhydroquinonyl, chlorohydroquinonyl, methoxyhydroquinonyl, 2,6-dimethylhydroquinonyl, 2,6-dimethoxyhydroquinonyl, 2-methoxy-6-methylhydroquinonyl, 2,3-dimethylhydroquinonyl, 2,5,6-trimethylhydroquinonyl, etc.

In a preferred embodiment, n in the above formula is 1, A is ethylene and Dev is a hydroquinone.

In addition to the Dev moiety being attached to the arylazo-pyrazolotriazole dye-releasing compound shown above, the ring structures shown may be substituted with various substituents. For example, if the Dev moiety is attached to the phenyl group, then the alternate position of attachment of Dev to the pyrazole ring can be substituted with alkyl of 1 to 6 carbon atoms, for example, while the triazole ring can be substituted with various substituents such as phenyl, phenyl substituted with alkyl of 1 to 4 carbon atoms, alkoxy, halogens, solubilizing groups such as sulfonamido, sulfamoyl, carboxy, sulfo, hydrolyzable precursors thereof, etc. Similarly, if Dev is attached to the triazole ring, then the phenyl group can be substituted with alkyl of 1 to 4 carbon atoms, alkoxy, halogen, solubilizing groups such as sulfonamido, sulfamoyl, carboxy, sulfo, hydrolyzable precursors thereof, etc., while the pyrazole ring can be substituted in the same manner as described above. If Dev is attached to the pyrazole ring, then the phenyl group and triazole ring can be substituted in the same manner described above. When Dev is attached to one of the positions in the phenyl group, the other positions may be substituted in the manner described above.

When hydrolyzable precursors of the dye moiety of the above compounds are employed, the absorption spectrum of the azo dye is shifted to shorter wavelengths. "Shifted dyes" of this type absorb light outside the range to which the associated silver halide layer is sensitive.

Representative compounds included within the scope of the invention include the following:

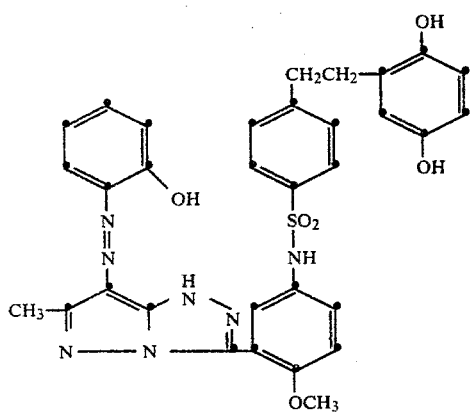
(1)
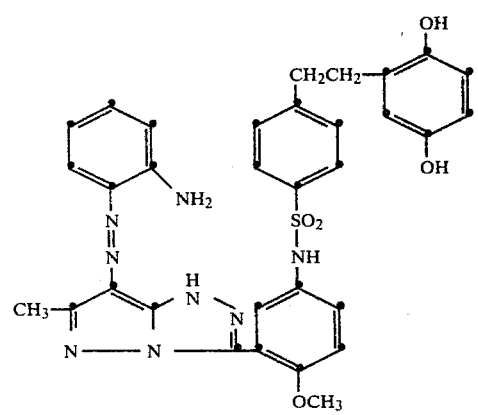
(2)
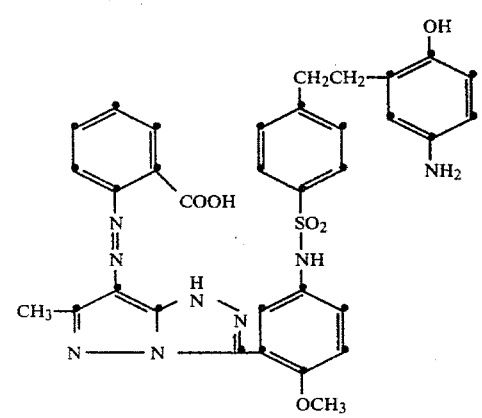
(3)
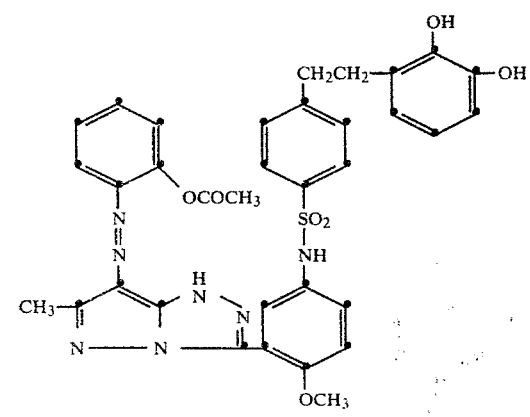
(4)

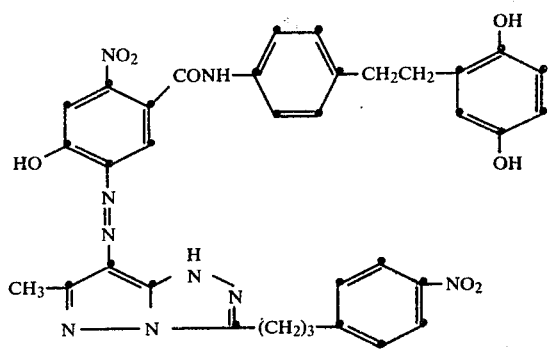
(5)
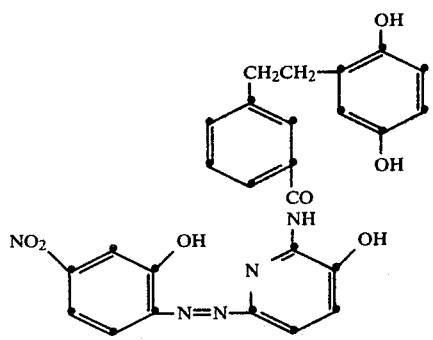
(6)
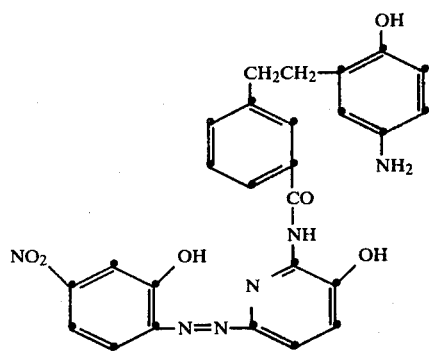
(7)
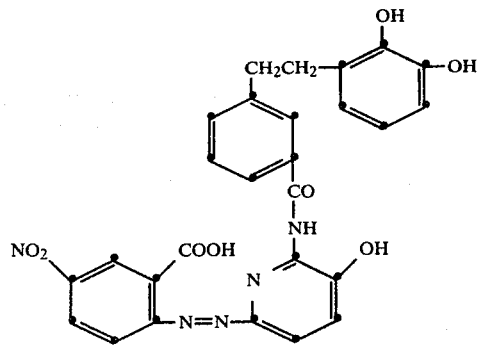
(8)
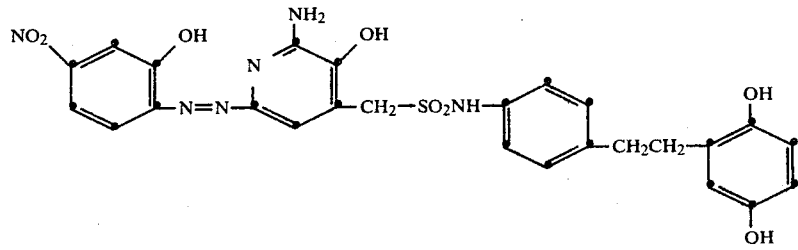
(9)

-continued
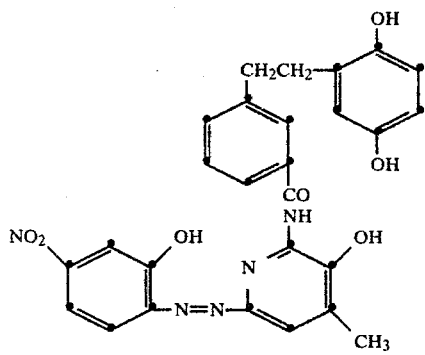 (10)
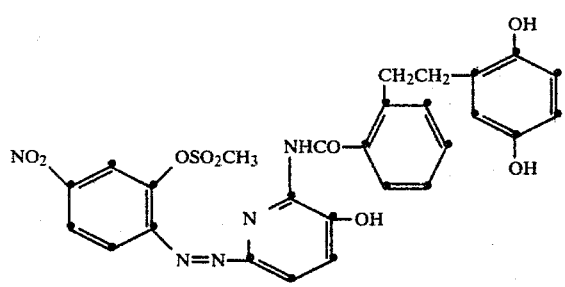 (11)
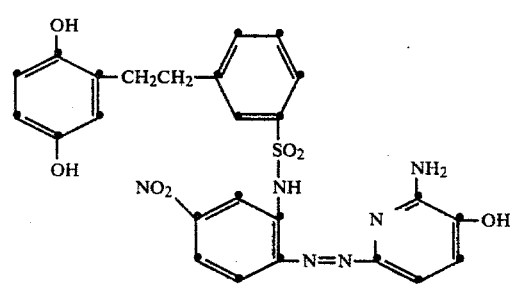 (12)
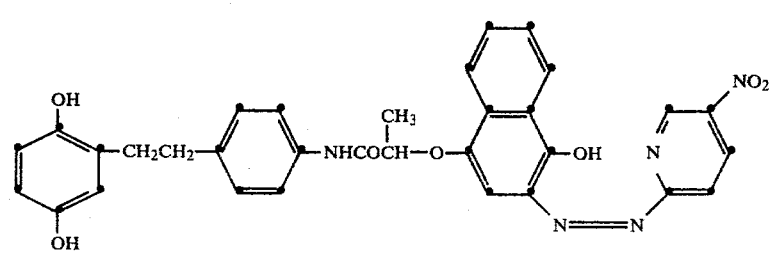 (13)
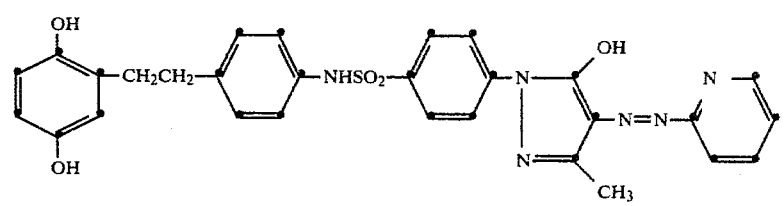 (14)
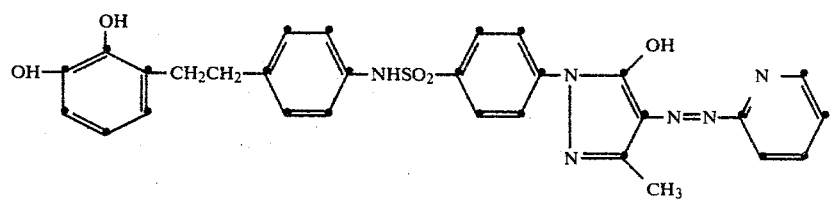 (15)

(16)

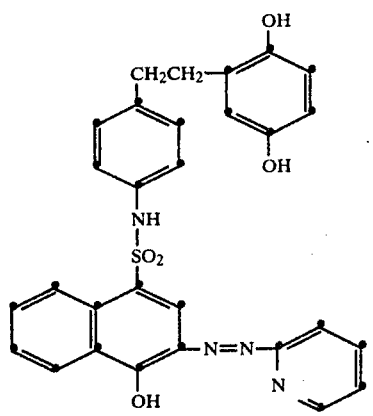

(17)

(18)

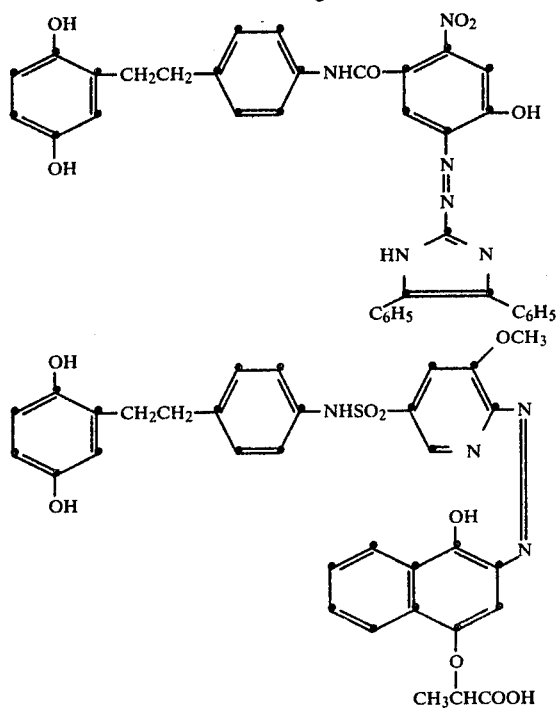

(19)

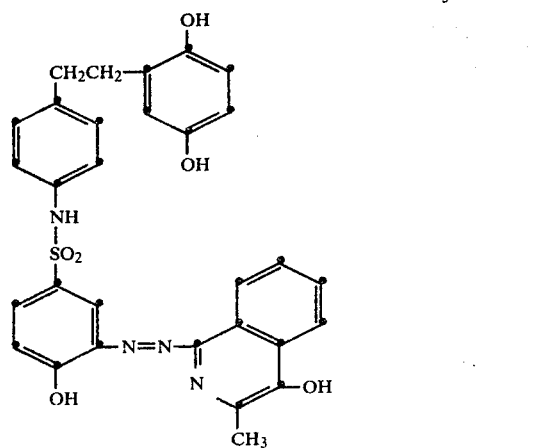

A process for producing a photographic transfer image in color according to our invention comprises:

(a) treating an imagewise-exposed photographic element as described above with an alkaline processing composition in the presence of a silver halide developing agent to effect development of each of the exposed silver halide emulsion layers, (b) forming an imagewise distribution of diffusible dye developer as a function of the imagewise exposure of each of the silver halide emulsion layers;

(c) at least a portion of the imagewise distribution of the dye developer diffusing to a dye image-receiving layer; and (d) contacting the imagewise distribution of the dye developer with metal ions, thereby forming a metal-complexed azo dye developer transfer image.

In a preferred embodiment of the invention, the tridentate azo dye developer will form a coordination complex in the image-receiving layer with polyvalent metal ions. The metal ions can be present in the image-receiving layer itself or in a layer adjacent thereto, or the image-receiving layer can be contacted with metal ions in a bath after diffusion of the dye has taken place. Metal ions most useful in the invention are those which: are essentially colorless when incorporated into the image-receiving element, are inert with respect to the silver halide layers, react readily with the dye developer to form a complex of the desired hue, are tightly coordinated to the dye in the complex, have a stable oxidation state, and form a dye complex which is stable to heat, light and chemical reagents. In general, good results are obtained with polyvalent metal ions such as copper (II), zinc (II), nickel (II), platinum (II), palladium (II) and cobalt (II) ions.

In another embodiment of the invention, the dye developers can be "pre-metallized", i.e., the coordination complex can be formed between the metal ions and the dye developer in the photosensitive element before exposure. While such compounds tend to be more bulky and take longer to diffuse to the image-receiving layer, they can be useful in some instances.

It is believed that the coordination complexes which are formed from the tridentate azo dye ligands according to the invention in one of the preferred embodiments thereof has the following structure:

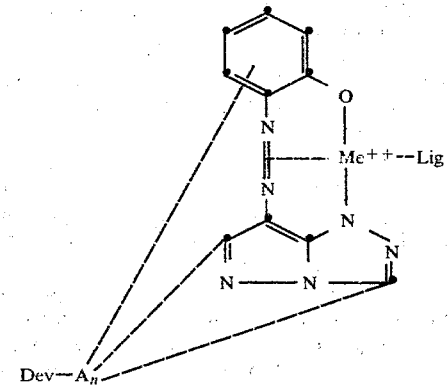

where Me is metal; Lig is one or more ligand groups, depending upon the coordination number of the metal ion, such as H$_2$O, Cl, pyridine, etc; Dev, A and n are as described above, Thus, in accordance with another embodiment of our invention, a photographic element is provided which comprises a support having thereon a coordination complex of a polyvalent metal ion and a compound having the formula:

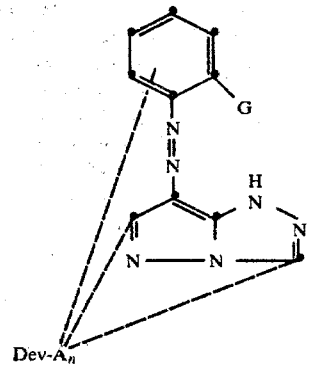

wherein G is a metal chelating group, e.g., those as described previously; Dev, A and n are as described above. The element usually contains a photographic mordant or image-receiving layer to bind the dye or coordination complex thereto.

The photographic element in the above-described process can be treated with an alkaline processing composition to effect or initiate development in any manner. A preferred method for applying processing composition is by use of a rupturable container or pod which contains the composition. In general, the processing composition employed in this invention contains the developing agent for development, although the composition could also be solely an alkaline solution where the developer is incorporated in the photographic element, the image-receiving element or the process sheet, in which case the alkaline solution serves to activate the incorporated developer.

A photographic film unit or assemblage in accordance with this invention is adapted to be processed by an alkaline processing composition, and comprises:

(1) a photographic element as described above; and
(2) a dye image-receiving layer.

In this embodiment, the processing composition may be inserted into the film unit, such as by interjecting processing solution with communicating members similar to hypodermic syringes which are attached either to a camera or camera cartridge. The processing composition may also be applied by means of a swab or by dipping in a bath, if so desired.

In a preferred embodiment of the invention, the assemblage itself contains the alkaline processing composition and means containing same for discharge within the film unit, such as a rupturable container which is adapted to be positioned during processing of the film unit so that a compressive force applied to the container by pressure-applying members, such as would be found in a camera designed for in-camera processing, will effect a discharge of the container's contents within the film unit.

In the embodiment described above, the dye image-receiving layer may itself contain metal ions, or the metal ions may be present in an adjacent layer, so that the tridentate azo dye developer will form a coordination complex therewith. The dye developer thus becomes immobilized in the dye image-receiving layer and metallized at the same time. Alternatively, the dye image in the dye image-receiving layer may be treated with a solution containing metal ions to effect metallization. The formation of the coordination complex shifts the absorption of the dye to the desired hue, usually to longer wavelengths, which have a different absorption than that of the initial dye developer compound. If this shift is large enough, then the dye developer compound may be incorporated in a silver halide emulsion layer without adversely affecting its sensitivity.

The dye image-receiving layer in the above-described film unit can be located on a separated support adapted to be superposed on the photographic element after exposure thereof. Such image-receiving elements are generally disclosed, for example, in U.S. Pat. No. 3,362,819. When the means for discharging the processing composition is a rupturable container, it is usually positioned in relation to the photographic element and the image-receiving element so that a compressive force applied to the container by pressure-applying members, such as would be found in a typical camera used for in-camera processing, will effect a discharge of the container's contents between the image-receiving element and the outermost layer of the photographic element. After processing, the dye image-receiving element is separated from the photographic element.

The dye image-receiving layer in the above-described film unit can also be located integral with the photographic element between the support and the lowermost photosensitive silver halide emulsion layer. One useful format for integral receiver-negative photographic elements is disclosed in Belgian Pat. No. 757,960. In such an embodiment, the support for the photographic element is transparent and is coated with an image-receiving layer, a substantially opaque light-reflective layer, e.g., $TiO_2$, and then the photosensitive layer or layers described above. After exposure of the photographic element, a rupturable container containing an alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer, and dye images, formed as a function of development, diffuse to the image-receiving layer to provide a positive, right-reading image which is viewed through the transparent support on the opaque reflecting layer background. For other details concerning the format of this particular integral film unit, reference is made to the above-mentioned Belgian Pat. No. 757,960.

Another format for integral negative-receiver photographic elements in which the present invention can be employed is disclosed in Belgian Pat. No. 757,959. In this embodiment, the support for the photographic element is transparent and is coated with the image-receiving layer, a substantially opaque, light-reflective layer and the photo-sensitive layer or layers described above. A rupturable container, containing an alkaline processing composition and an opacifier, is positioned between the top layer and a transparent cover sheet which has thereon a neutralizing layer and a timing layer. The film unit is placed in a camera, exposed through the transparent cover sheet and then passed through a pair of pressure-applying members in the camera as it is being removed therefrom. The pressure-applying members rupture the container and spread processing composition and opacifier over the negative portion of the film unit to render it light-sensitive. The processing composition develops each silver halide layer and dye images, formed as a result of development, diffuse to the image-receiving layer to provide a positive, right-reading image which is viewed through the transparent support on the opaque reflecting layer background. For further details concerning the format of this particular integral film unit, reference ot made to the above-mentioned Belgian Pat. No. 757,959.

Still other useful integral formats in which this invention can be employed are described in U.S. Pat. Nos. 3,415,644; 3,415,645; 3,415,646; 3,647,437; and 3,635,707. In most of these formats a photosensitive silver halide emulsion is coated on an opaque support, and a dye image-receiving layer is located on a separate transparent support superposed over the layer outermost from the opaque support. In addition, this transparent support also preferably contains a neutralizing layer and a timing layer underneath the dye image-receiving layer.

The film unit or assembly of the present invention may be used to produce positive images in single- or multicolors. In a three-color system, each silver halide emulsion layer of the film assembly will have associated therewith a dye developer which possesses a predominant spectral absorption within the region of the visible spectrum to which said silver halide emulsion is sensitive, i.e., the blue-sensitive halide emulsion layer will have a yellow dye developer associated therewith, the green-sensitive silver halide emulsion layer will have a magenta dye developer associated therewith, and the red-sensitive silver halide emulsion layer will have a cyan dye developer associated therewith. The dye developer associated with each silver halide emulsion layer may be container either in the silver halide emulsion layer itself or in a layer contiguous to the silver halide emulsion layer, i.e., the dye developer may be coated in a separate layer underneath the silver halide emulsion layer with respect to the exposure direction.

Our novel dye developers may be employed in combination with any other suitable dye developers in a three-color photosensitive element of the invention. Dye developers, i.e., compounds which contain in the same molecule both the chromophoric system of a dye and also a silver halide developing function, and their functioning in color diffusion transfer systems in general are well known in the art as shown, for example, by U.S. Pat. Nos. 2,983,606; 2,992,106; 3,047,386; 3,076,808; 3,076,820; 3,077,402; 3,126,280; 3,131,061; 3,134,762; 3,134,765; 3,135,604; 3,135,605; 3,135,606; 3,135,734; 3,141,772 and 3,142,565.

The concentration of the dye developer that is employed in the present invention may be varied over a wide range, depending upon the particular compound employed and the results desired. For example, the dye developer may be coated in a layer at a concentration of 0.1 to 3 $g/m^2$. The dye developer may be dispersed in a hydrophilic film-forming natural material or synthetic polymer, such as gelatin, polyvinyl alcohol, etc, which is adapted to be permeated by aqueous alkaline processing composition.

The liquid processing composition employed in the invention may contain one or more auxiliary or accelerating silver halide developing agents, such as p-methylaminophenyl (Metol); 2,4-diaminophenol (Amidol); benzylaminophenol; hydroquinone; a substituted hydroquinone such as toluhydroquinone, phenylhydroquinone or 4'-methylphenylhydroquinone; or a 3-pyrazolidone such as 1-phenyl-3-pyrazolidone. These silver halide developing agents are substantially colorless, at least in their unoxidized form. It is possible that some of the dye developer oxidized in exposed areas may be oxidized by an energy transfer reaction with oxidized auxiliary developing agent.

In addition, development may be effected in the presence of an onium compound, particularly a quaternary ammonium compound, in accordance with the processes in U.S. Pat. Nos. 3,173,786 and 3,146,102.

In addition to conventional techniques for the direct dispersion of a particulate solid material in a polymeric or colloidal matrix, such as ball-milling and the like techniques, the preparation of a dye developer dispersion can also be obtained by dissolving the dye developer in an appropriate solvent or mixture of solvents, dispersing the resultant solution in the polymeric binder, with optional subsequent removal of the solvent or solvents employed. Further details concerning these dispersing techniques and the solvents employed are found, for example, in U.S. Pat. Nos. 2,269,158; 2,322,027; 2,304,939; 2,304,940; 2,801,171 and the like.

The various silver halide emulsion layers of a color film assembly employed in this invention can be disposed in the usual order, i.e., the blue-sensitive silver halide emulsion layer first with respect to the exposure side, followed by the green-sensitive and red-sensitive silve halide emulsion layers. If desire,d, a yellow dye layer or a yellow colloidal silver layer can be present between the blue-sensitive and green-sensitive silver halide emulsion layers for absorbing or filtering blue radiation that may be transmitted through the blue-sensitive layer. If desired, the selectively sensitized silver halide emulsion layers can be disposed in a different order, e.g., the blue-sensitive layer first with respect to the exposure side, followed by the red-sensitive and green-sensitive layers.

The rupturable container employed in certain embodiments of this invention can be of the type disclosed in U.S. Pat. Nos. 2,543,181; 2,643,886; 2,653,732; 2,723,051; 3,056,492; 3,056,491 and 3,152,515. In general, such containers comprise a rectangular sheet of fluid- and air-impervious material folded longitudinally upon itself to form two walls which are sealed to one another along their longitudinal and end margins to form a cavity in which processing solution is contained.

Generally speaking, except where noted otherwise, the silver halide emulsion layers employed in the invention comprise photosensitive silver halide dispersed in gelatin and are about 0.6 to 6 microns in thickness; the dye developers are dispersed in an aqueous alkaline solution-permeable polymeric binder, such as gelatin, as a separate layer about 0.2 to 7 microns in thickness; and the alkaline solution-permeable polymeric interlayers, e.g., gelatin, are about 0.2 to 5 microns in thickness. Of course, these thicknesses are approximate only and can be modified according to the product desired.

Any material can be employed as the image-receiving layer in this invention as long as the desired function of mordanting or otherwise fixing the dye images is obtained. As examples of useful image-receiving materials, mention may be made of nylon, e.g., N-methoxymethylpolyhexamethylene adipamide, polyvinyl alcohol, and gelatin, particularly polyvinyl alcohol or gelatin containing a dye mordant such as poly-4-vinylpyridine. The image-receiving element also may contain a development restrainer, e.g., 2-phenyl-5-mercaptotetrazole, as disclosed in U.S. Pat. No. 3,265,498.

Use of a pH-lowering material in the film units of this invention will usually increase the stability of the transferred image. Generally, the pH-lowering material will effect a reduction in the pH of the image layer from about 13 to 14 to at least 11 and preferably 5 to 8 within a short time after imbibition. Suitable material and their functions are disclosed on pages 22 and 23 of the July 1974 edition of *Research Disclosure*, and pages 35 through 37 of the July 1975 edition of *Research Disclosure*, the disclosures of which are hereby incorporated by reference.

A timing or inert spacer layer can be employed in the practice of this invention over the pH-lowering layer which "times" or controls the pH reduction as a function of the rate at which the alkaline composition diffuses through the inert spacer layer. Examples of such timing layers and their functions are disclosed in the *Research Disclosure* articles mentioned in the paragraph above concerning pH-lowering layers.

The alkaline processing composition employed in this invention is the conventional aqueous solution of an alkaline material, e.g., alkali metal hydroxides or carbonates such as sodium hydroxide, sodium carbonate or an amine such as diethylamine, preferably possessing a pH in excess of 11, and preferably containing a developing agent as described previously. Suitable materials and addenda frequently added to such compositions are disclosed on pages 79 and 80 of the November 1976 edition of *Research Disclosure*, the disclosure of which is hereby incorporated by reference.

The alkaline solution-permeable, substantially opaque, light-reflective layer employed in certain embodiments of photographic film units used in this invention are described more fully in the November 1976 edition of *Research Disclosure*, page 82, the disclosure of which is hereby incorporated by reference.

The supports for the photographic elements used in this invention can be any material, as long as it does not deleteriously affect the photographic properties of the film unit and is dimensionally stable. Typical flexible sheet materials are described on page 85 of the November 1976 edition of *Research Disclosure*, the disclosure of which is hereby incorporated by reference.

While the invention has been described with reference to layers of silver halide emulsions and dye image-providing materials, dotwise coating, such as would be obtained using a gravure printing technique, could also be employed. In this technique, small dots of blue-, green- and red-sensitive emulsions have associated therewith, respectively, dots of yellow, magenta and cyan color-providing substances. After development, the transferred dyes would tend to fuse together into a continuous tone.

The silver halide emulsions useful in this invention, both negative-working and direct-positive ones, are well known to those skilled in the art and are described in *Product Licensing Index*, Volume 92, December 1971, publication 9232, page 107, paragraph I, "Emulsion types"; they may be chemically and spectrally sensitized as described on page 107, paragraph III, "Chemical sensitization", and pages 108 and 109, paragraph XV, "Spectral sensitization", of the above article; they can be protected against the production of fog and can be stabilized against loss of sensitivity during keeping by employing the materials described on page 107, paragraph V, "Antifoggants and stabilizers", of the above article; they can contain development modifiers, hardeners, and coating aids as described on pages 107 and 108, paragraph IV, "Development modifiers"; paragraph VII, "Hardeners"; and paragraph XII, "Coating aids", of the above article; they and other layers in the photographic elements used in this invention can contain plasticizers, vehicles and filter dyes described on page 108, paragragh XI, "Plasticizers and lubricants", and paragraph VIII, "Vehicles", and page 109, paragraph XVI, "Absorbing and filter dyes", of the above article; they and other layers in the photographic elements used in this invention may contain addenda which are incorporated by using the procedures described on page 109, paragraph XVII, "Methods of addition", of the above article; and they can be coated by using the various techniques described on page 109, paragraph XVIII, "Coating procedures", of the above article, the disclosure of which are hereby incorporated by reference.

The term "nondiffusing" used herein has the meaning commonly applied to the term in photography and denotes materials that for all practical purposes do not migrate or wander through organic colloid layers, such as gelatin, in the photographic elements of the invention in an alkaline medium and preferably when processed in a medium having a pH of 11 or greater. The same meaning is to be attached to the term "immobile". The term "diffusible" as applied to the materials of this invention has the converse meaning and denotes materials having the property of diffusing effectively through the colloid layers of the photographic elements in an alkaline medium. "Mobile" has the same meaning as "diffusible".

The term "associated therewith" as used herein is intended to mean that the materials can be in either the same or different layers so long as the materials are accessible to one another.

The novel compounds herein disclosed are also suitable for use as dyes for textile fibers, such as nylon.

The following examples are provided to further illustrate the invention.

EXAMPLE 1

Preparation of Compound 5

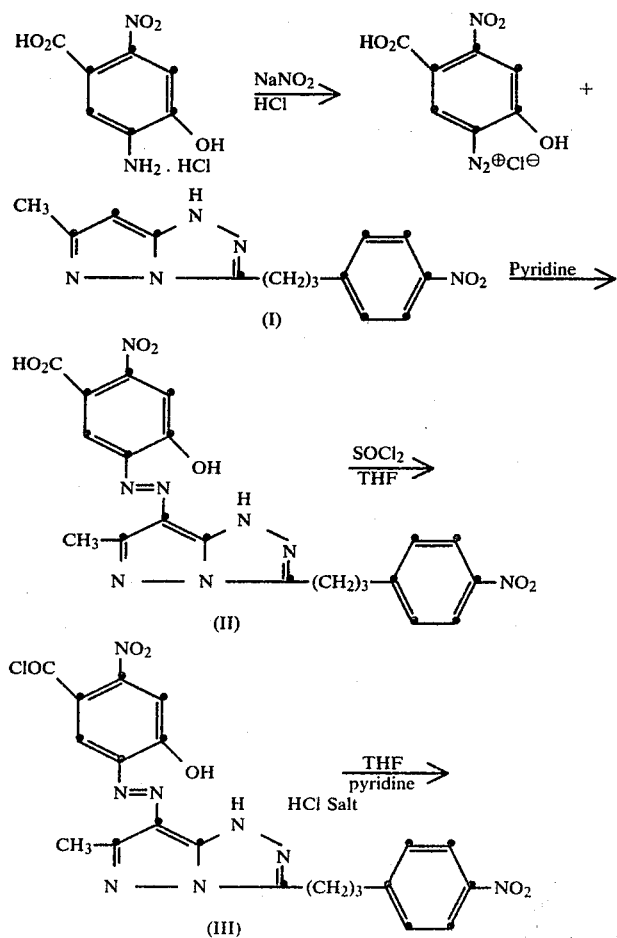

-continued

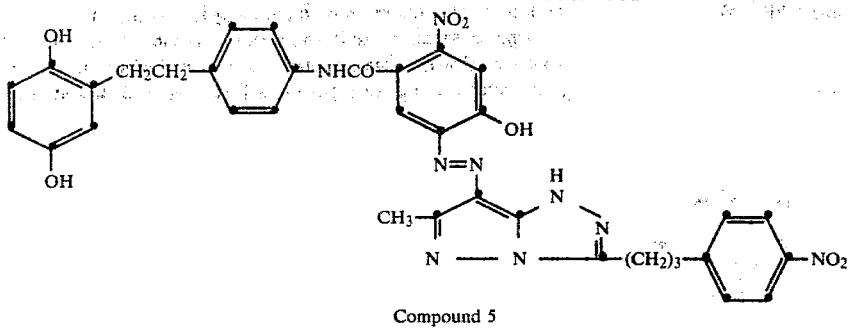

Compound 5

(a) Preparation of
4-Hydroxy-5-{6-methyl-3-[3-(4-nitrophenyl)propyl]-1H-pyrazolo[3,2-c]-s-triazol-7-ylazo}-2-nitrobenzoic acid (II)

(1) Diazotization

A solution of sodium nitride (3.5 g, 0.05 M) in water (25 ml) was slowly added to a stirred solution of 5 -carboxy-2-hydroxy-4-nitroanilinium chloride (11.8 g, 0.05 M) in concentrated hydrochloric acid (10 ml) and water (200 ml) cooled to 5° C. This suspension was stirred at 5° C. for one half-hour.

(2) Formation of the Azo Dye

A solution of sodium hydroxide (10.0 g, 0.2 M) in water (100 ml) was added to a stirred solution of the pyrazolotriazole (I) (14.3 g, 0.05 M) in pyridine (650 ml).

The diazonium salt suspension (from Part 1) was slowly added, with stirring to the cooled (5° C.) coupler solution to give a purple solution which was stirred overnight. The solution was poured into a stirred mixture of concentrated hydrochloric acid (400 ml) and water (3 liters). The resulting yellow solid was filtered off and recrystallized from a mixture of ethanol (200 ml) and tetrahydrofuran (250 ml) to give, after drying at 50° C., Compound II (21.2 g).

(B) Preparation of
7-(5-Chlorocarbonyl-2-hydroxy-4-nitrophenylazo)-6-methyl-3-[3-(4-nitrophenyl)-propyl]-1H-pyrazolo[3,2-c]-s-triazol-1-inium chloride (III)

Thionyl chloride (50 ml) was added with stirring to a suspension of the dye II in dry tetrahydrofuran (50 ml). The mixture became warm and the suspension dissolved, giving an orange-red solution. After a few minutes, an orange solid precipitated. The mixture was stirred for a further 15 minutes, cooled to 5° C. and the product filtered off and dried at 50° C.

(c) Preparation of
4-Hydroxy-N-{4-[2-(2,5-dihydroxy-pheynl)ethyl]-phenyl}-5-{6-methyl-3-[3-(4-nitrophenyl)propyl]-1H-pyrazolo[3,2-c]-s-triazol-7-ylazo}-2-nitrobenzamide (5)

Pyridine (1.1 g, 0.015 mole) was added to a stirred suspension of the hydrochloride III (3.9 g) and 2-(4-aminophenethyl)hydroquinone (1.7 g, 0.007 mole) in dry THF under nitrogen at room temperature. The mixture was stirred for 1 hour and the crude product (5.0 g) isolated by filtration. This solid was slurried with methanol (50 ml), stirred overnight and the purified product collected by filtration (yield, 3.3 g).

EXAMPLE 2

Preparation of Compound 13

A solution of 2-p-aminophenethylhydroquinone (2.28 g, 9.9 mmoles) in tetrahydrofuran (25 ml) was combined with a solution of 4-[1-chloroformyl)ethoxy]-2-(5-nitro-2-pyridylazo)-1-naphthol (3.97 g, 9.9 mmoles), tetrahydrofuran (25 ml) and pyridine (1 ml), and allowed to react with stirring for approximately 15 hours. The supernatant was decanted from a gummy material, concentrated in vacuo to a gummy residue which was slurried with distilled water to cause solidification; the solid was collected by filtration, washed with water and air dried; yield, 3.10 g. The crude product was dissolved in tetrahydrofuran and chromatographed on silica gel using the following solvents in order as eluting agents: (a) dichloromethane, (b) dichloromethan/methanol (99:1), and (c) dichloromethane/methanol (95:5). Fractions (a) and (b) were discarded; Fraction (c) was concentrated in vacuo to a residue to obtain a crude sample of Compound 13; yield, 1.0 g.

The original gummy residue remaining in the reaction vessel after decantation of the tetrahydrofuran supernatant was treated in the same manner to obtain another 1.74 g of Compound 13; total yield of crude product was 2.74 g. The crude product was recrystallized from acetic acid (55 ml); yield, 2.66 g (42 percent).

EXAMPLE 3

Preparation of Compound 14

1-p-(Chlorosulfonyl)phenyl-3-methyl-4-(2-pyridylazo)-2-pyrazolin-5-one (1.2 g, 3.2 mmoles) was added to a solution of 2 -p-aminophenethylhydroquinone (0.7 g, 3.1 mmoles) in pyridine (10 ml) under a nitrogen atmosphere at room temperature. After 15 minutes, the reaction mixture was poured onto ice/HCl, stirred and filtered to obtain a residue which was dried in vacuo. The product was recrystallized from ethanol/HCl to yield pure Compound 14.

EXAMPLE 4

Preparation of Compound 16

4-Benzoyloxy-3-(2-pyridylazo)-1-naphthalenesulfonyl chloride (17.0 g, 37.5 mmoles) and 2-p-aminophenethylhydroquinone (17.0 g, 74.2 mmoles) were combined in pyridine (500 ml), stirred in an ice bath for one hour, and allowed to stand overnight for approximately 15 hours. The reaction mixture was poured onto ice/HCl to form a semi-solid precipitate. The water was decanted, and the semi-solid mass was triturated with methanol to provide a precipitate which was collected by filtration, washed with methanol and dried in vacuo; yield, 16.0 g (59.7 percent) of Compound 16.

EXAMPLE 5

Preparation of Compound 17

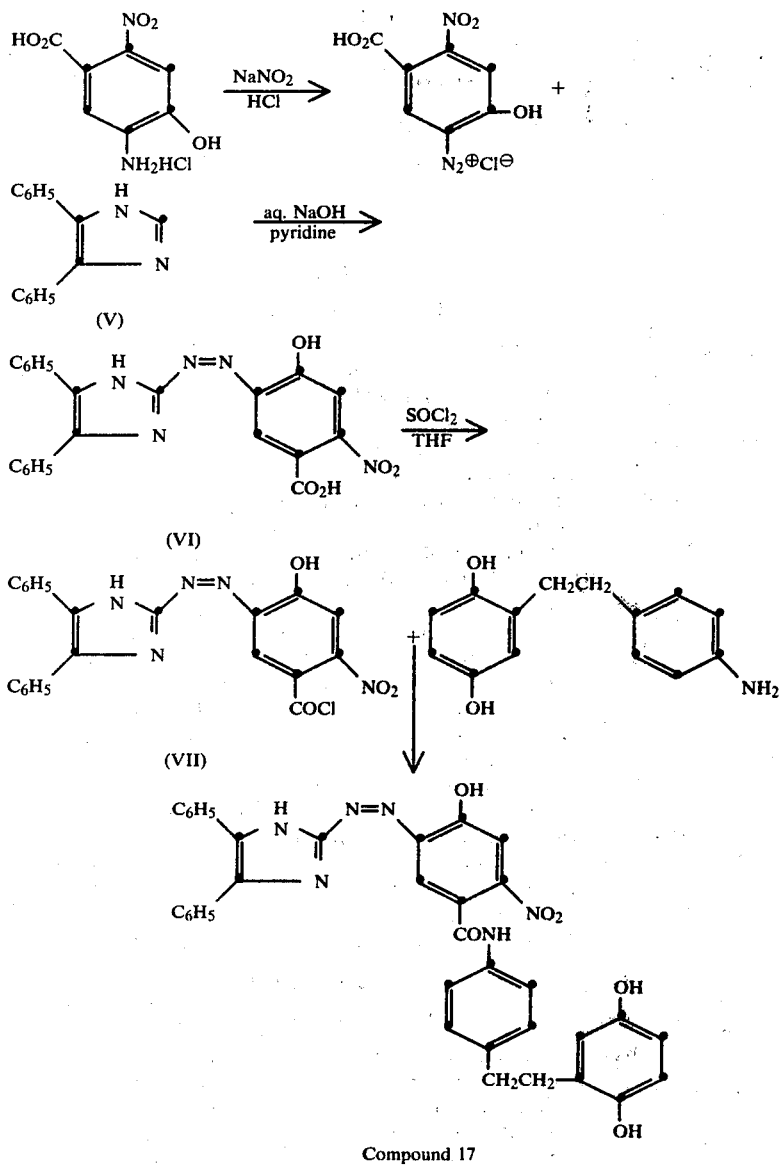

Compound 17

(A) Preparation of 4-Hydroxy-2-nitro-5-(4,5-diphenylimidazol-2-ylazo) Benzoic Acid (VI)

(1) Diazotization

A solution of sodium nitrite (3.45 g, 0.05 mole) in water (20 ml) was slowly added to a stirred solution of 5-carboxy-2-hydroxy-4-nitro-anilinium chloride (11.47 g, 0.049 mole) in concentrated hydrochloric acid (10 ml) and water (200 ml) cooled to 5° C. A fluffy yellow solid precipitated from solution. This suspension was stirred at 5° C. for 20 minutes before being used.

(2) Formation of Azo Dye

A solution of sodium hydroxide (9.8 g, 0.24 mole) in water (100 ml) was added intermittently with water (200 ml total) to a stirred solution of 4,5-diphenylimidazole (11.0 g, 0.05 mole) in pyridine (250 ml) to give a clear one-phase coupler solution.

The diazonium salt suspension (from Part 1) was slowly added, with stirring, to the cooled (5° C.) coupler solution to give a purple solution which was stirred at room temperature for 3 days.

The solution was filtered, poured into a stirred mixture of concentrated hydrochloric acid (650 ml) and water (4 liters) and the red solid filtered off and dried at 50° C. TLC analysis showed the product to be pure. The yield of product was 16.2 g, 77 percent.

(B) Preparation of 4-Hydroxy-2-nitro-5-(4,5-diphenylimidazol-2-ylazo) Benzoyl Choloride (VII)

Thionyl chloride (120 ml) was added with stirring to a suspension of VI (11.1 g, 0.026 mole) in dry tetrahydrofuran (120 ml) at 20° C. The mixture became warm and the suspension dissolved giving a dark-red solution. After a few minutes, a bright-red solid precipitated. The mixture was stirred for a further 15 minutes, cooled to 5° C. and the product filtered off and dried at 50° C. for one hour. TLC analysis showed the product to be pure.

The yield was 10.2 g, 88 percent.

(C) Preparation of
4-Hydroxy-N-{4-[2-(2,5-dihydroxy-phenyl)ethyl]-phenyl}-2-nitro-5-(4,5-diphenylimidazol-2-ylazo)benzamide (17)

Pyridine (0.8 g, 0.01 mole) was added to a stirred mixture of VII (3.1 g, 0.007 mole) and 2-(4-aminophenethyl)hydroquinone (1.7 g, 0.007 mole) in dry THF under nitrogen at 20° C.

The mixture was stirred for one and one-half hours and the crude product isolated by filtration. This solid was slurried with methanol (50 ml) for 15 hours, and the purified product recovered by filtration and dried in air at 50° C. The dye was found to contain one mole of water of crystallization. (Yield, 2.5 g.)

EXAMPLE 6

Preparation of Compound 18

4-(1-Carboxyethoxy)-1,2-naphthoquinone (6.72 g, 27.3 mmoles) was added to a solution of 2-hydroazino-N-[4-{2-(2,5-dihydroxyphenyl)ethyl}phenyl]-3-methoxypyridine-5-sulfonamide (11.74 g, 27.3 mmoles) in acetic acid (330 ml) and the reaction mixture was stirred for approximately 18 hours at room temperature. The solid which formed was collected by filtration, washed with acetic acid, then water, and air dried; yield, 6.05 g. The crude product was extracted with boiling acetonitrile; the residue remaining weighted 3.44 g. The acetonitrile extract was cooled to yield another 2.51 g of Compound 18; total yield, 5.95 g (33.1 percent).

EXAMPLE 7

Photographic Test—Compounds 5, 13, 14, 16, 17, and 18

The following image transfer elements were prepared by coating the following layers in the order recited on an opaque cellulose acetate film support. Quantities are parenthetically given in g/m² unless otherwise stated.

(1) Subbing layer of gelatin (1.08);
(2) Dye Developer Compound (see Table) (0.32) disperation, and gelatin (2.15);
(3) Blue-sensitive silver bromo-iodide emulsion (1.35 g Ag/m²), gelatin (1.08) and 4-hydroxy-6-methyl-1,3,3A,7-tetraazaindine (2); and
(4) p-tolylhydroquinone (0.11) and gelatin (0.98).

Samples of the above-prepared photosensitive elements were exposed (1/50″, 500W, CF 4.08, 6100° K.). The exposed samples were then processed at 22° C. by rupturing a pod containing a viscous processing composition between the photosensitive element and two receiving elements, as described below, by passing the "sandwich" between a pair of juxtaposed rollers so that the processing composition layer was about 0.0038 inch.

The processing composition was as follows:

| Distilled water | 1272 g |
| Carbon black | 319.5 g |
| Potassium hydroxide (88.5 percent) | 189.8 g |
| Benzotriazole | 15.0 g |
| Hydroxyethylcellulose (Natrosol 250HH) | 51.0 g |
| N-benzyl-α-picolinium bromide (50 percent by weight) | 45.0 g |

Receiving element (A) consisted of a transparent cellulose acetate support having coated thereon:

(1) Hardened deionized bone gelatin (1.08);
(2) Receiving layer of hardened deionized bone gelatin (2.16) and polyvinylpyridine (2.16);
(3) Titanium dioxide (16.14) and bone gelatin (2.58);
(4) Carbon black (1.88) and bone gelatin (1.24); and
(5) Bone gelatin (1.18).

Receiving element (B) was the same as (A), except that layer (1) also contained $NiSO_4 \cdot 6H_2O$ (0.58) as a chelating metal salt.

After a ten-minute transfer time, the receivers were peeled apart from the negatives, washed with water to remove excess processing materal and dried. Reflectance spectra of the receivers were then obtained. The receivers were then subjected to a high-intensity light (5000 foot-candles) and reflectance spectra obtained after 2, 4, 8 and 16 days to measure the loss in $D_{max}$. The following data were obtained:

TABLE

| Dye Developer In Photographic Element | Metallized Receiver | $\lambda_{max}$ (nm) | $D_{max}$ | $\Delta D_{max}$ 2 days | 4 days | 8 days | 16 days |
| --- | --- | --- | --- | --- | --- | --- | --- |
| Compound 5 | No | 542 | 0.57 | −0.30 | −0.35 | −0.57 | −0.57 |
| Compound 5 | Yes | 510 | 0.48 | −0.08 | −0.09 | −0.12 | −0.15 |
| Compound 13 | No | 592 | 0.83 | −0.49 | −0.56 | −0.83 | −0.83 |
| Compound 13 | Yes | 632 | 0.97 | −0.15 | −0.21 | −0.28 | −0.36 |
| Compound 14 | No | 410 | 1.10 | −0.16 | −0.22 | −0.36 | −0.46 |
| Compound 14 | Yes | 444 | 1.10 | −0.03 | −0.05 | −0.08 | −0.11 |
| Compound 16 | No | 518 | 1.53 | −0.67 | −0.85 | −1.02 | −1.14 |
| Compound 16 | Yes | 540 | 1.56 | −0.04 | −0.04 | −0.09 | −0.13 |
| Compound 17 | No | 558 | 0.92 | −0.56 | −0.65 | −0.92 | −0.92 |
| Compound 17 | Yes | 598 | 0.84 | −0.11 | −0.16 | −0.23 | −0.32 |
| Compound 18 | No | 558 | 0.62 | −0.28 | −0.35 | −0.40 | −0.62 |
| Compound 18 | Yes | 659 | 0.77 | −0.09 | −0.10 | −0.14 | −0.17 |

The above data indicate that:
(1) The dye developers diffused to the receiver in an imagewise distribution as a function of exposure and development;
(2) The dye developers had metallizable chromophores and chelated with nickel ions in the receiver;
(3) The metallized dyes, except for Compound 5, exhibited a bathochromic shift; and
(4) The metallized dyes had greatly enhanced light stability.

The invention has been described in detail with particular reference to preferred embodiments thereof, but it will be understood that variations and modifications can be effected within the spirit and scope of the invention.

What is claimed is:

1. In a photographic element comprising a support having thereon at least one photosensitive silver halide emulsion layer, said emulsion layer having associated therewith a diffusible dye developer compound, the improvement wherein said dye developer compound has the following formula:

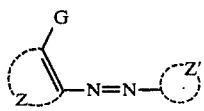

wherein:

Z represents the atoms necessary to complete a phenyl group;

Z' represents a pyrazolotriazole nucleus;

G is a metal chelating group, a salt thereof or a hydrolyzable precursor thereof; said compound also containing a silver halide developing moiety which is capable of developing an exposed silver halide emulsion under photographic processing conditions.

2. The photographic element of claim 1 wherein G is hydroxy; amino; carboxy; sulfonamido; sulfamoyl; a hydrolyzable ester group having the formula -OCOR$^1$, —OCOOR$^1$, —OCON(R$^1$)$_2$ or —COOR$^1$, wherein R$^1$ is an alkyl group having 1 to about 4 carbon atoms or an aryl group having 6 to about 8 carbon atoms.

3. The photographic element of claim 1 wherein said silver halide developing moiety is either a benzene or naphthalene radical which is substituted by at least two groups selected from the group consisting of hydroxyl and amino groups which are situated ortho or para to each other so as to be capable of developing an exposed silver halide emulsion.

4. In a photographic element comprising a support having thereon at least one photosensitive silver halide emulsion layer, said emulsion layer having associated therewith a diffusible dye developer compound, the improvement wherein said dye developer compound has a 7-arylazo-pyrazolotriazole dye moiety, said compound containing:

(a) in the ortho position of the arylazo moiety a metal chelating group, a salt thereof or a hydrolyzable precursor thereof, and (b) a silver halide developing moiety which is capable of developing an exposed silver halide emulsion under photographic processing conditions.

5. The photographic element of claim 4, wherein said compound has the formula:

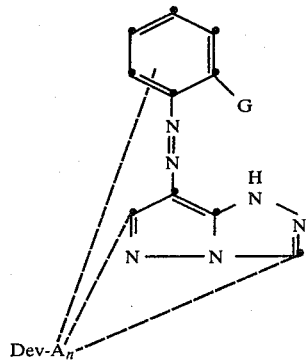

wherein:

G is a metal chelating group, a salt thereof or a hydrolyzable precursor thereof;

A is an organic divalent linking radical;

n is either 0 or 1; and

Dev is said silver halide developing moiety which is a dihydroxyphenyl substituent.

6. The photographic element of claim 5 wherein G is hydroxy; amino; carboxy; sulfonamido; sulfamoyl; or a hydrolyzable ester group having the formula —OCOR$^1$, —OCOOR$^1$, —OCON(R$^1$)$_2$ or —COOR$^1$, wherein R$^1$ is an alkyl group having 1 to about 4 carbon atoms or an aryl group having 6 to about 8 carbon atoms.

7. The photographic element of claim 5 wherein A is ethylene, n is 1 and Dev is a hydroquinone.

8. The photographic element of claim 4 wherein said dye developer compound is:

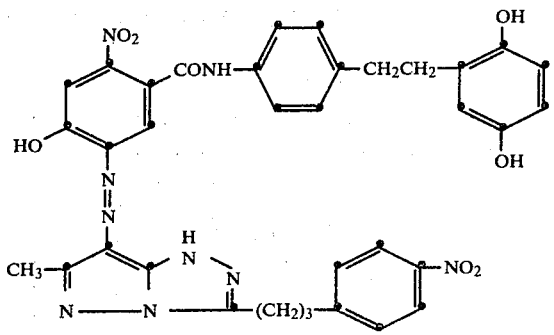

9. In a photographic element comprising a support having thereon a red-sensitive silver halide emulsion layer having a diffusible cyan dye developer associated therewith, a green-sensitive silver halide emulsion layer having a diffusible magenta dye developer associated therewith, and a blue-sensitive silver halide emulsion layer having a diffusible yellow dye developer associated therewith, the improvement wherein at least one of said dye developers has the following formula:

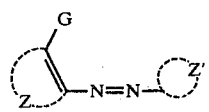

wherein:

Z represents the atoms necessary to complete a phenyl group;

Z' represents a pyrazolotriazole nucleus;

G is a metal chelating group, a salt thereof or a hydrolyzable precursor thereof;

said compound also containing a silver halide developing moiety which is capable of developing an exposed silver halide emulsion under photographic processing conditions.

10. In a photographic assemblage to be processed by an alkaline processing composition, said assemblage comprising:

(a) a photographic element comprising a support having thereon at least one photosensitive silver halide emulsion layer having associated therewith a diffusible dye developer compound; and (b) a dye image-receiving layer; the improvement wherein said dye developer has the following formula:

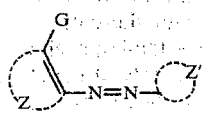

wherein:
Z represents the atoms necessary to complete a phenyl group;
Z' represents a pyrazolotriazole nucleus;
G is a metal chelating group, a salt thereof or a hydrolyzable precursor thereof;
said compound also containing a silver halide developing moiety which is capable of developing an exposed silver halide emulsion under photographic processing conditions, and wherein said dye image-receiving layer or a layer adjacent thereto contains metal ions.

11. In a photographic assemblage comprising:
(a) a photographic element comprising a support having thereon at least one photosensitive silver halide emulsion layer having associated therewith a diffusible dye developer compound;
(b) a dye image-receiving layer; and
(c) an alkaline processing composition and means for discharging same within said assemblage;
said assemblage containing a silver halide developing agent, the improvement wherein said dye developer has the following formula:

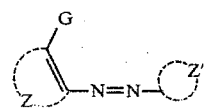

wherein:
Z represents the atoms necessary to complete a phenyl group;
Z' represents a pyrazolotriazole nucleus;
G is a metal chelating group, a salt thereof or a hydrolyzable precursor thereof; said compound also containing a silver halide developing moiety which is capable of developing an exposed silver halide emulsion under photographic processing conditions, and wherein said dye image-receiving layer or a layer adjacent thereto contains metal ions.

12. The photographic assemblage of claim 11 wherein Z represents the atoms necessary to complete a phenyl group and Z' represents a pyrazolotriazole nucleus.

13. The photographic assemblage of claim 11 wherein G is hydroxy; amino; carboxy; sulfonamido; sulfamoyl; a hydrolyzable ester group having the formula —O—COR$^1$, —OCOOR$^1$, —OCON(R$^1$)$_2$ or —COOR$^1$, wherein R$^1$ is an alkyl group having 1 to about 4 carbon atoms or an aryl group having 6 to about 8 carbon atoms.

14. The photographic assemblage of claim 11 wherein said silver halide developing moiety is either a benzene or naphthalene radical which is substituted by at least two groups selected from the group consisting of hydroxyl and amino groups which are situated ortho or para to each other so as to be capable of developing an exposed silver halide emulsion.

15. The photographic assemblage of claim 11 wherein:
(a) said dye image-receiving layer is located between said support and said silver halide emulsion layer; and
(b) said assemblage also includes a transparent cover sheet over the layer outermost from said support.

16. The photographic assemblage of claim 15 wherein said cover sheet has thereon, in sequence, a neutralizing layer and a timing layer.

17. The photographic assemblage of claim 16 wherein said discharging means is a rupturable container containing said alkaline processing composition and an opacifying agent, said container being so positioned during processing of said assemblage that a compressive force applied to said container will effect a discharge of the container's contents between said transparent sheet and the layer outermost from said support.

18. The photographic assemblage of claim 11 wherein said support having thereon said photosensitive silver halide emulsion layer is opaque and said dye image-receiving layer is located on a separate transparent support superposed over the layer outermost from said opaque support.

19. The photograpic assemblage of claim 18 wherein said transparent support has thereon, in sequence, a neutralizing layer, a timing layer, and said dye image-receiving layer.

20. The photographic assemblage of claim 11 wherein said dye developer compound has a 7-arylazo-pyrazolotriazole dye moiety, said compound containing said G moiety in the ortho position of the arylazo moiety.

21. The photographic assemblage of claim 20 wherein said compound has the formula:

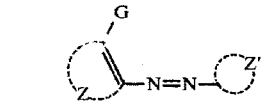

wherein:
G is a metal chelating group, a salt thereof or a hydrolyzable precursor thereof;
A is an organic divalent linking radical;
n is either 0 or 1; and
Dev is said silver halide developing moiety which is a dihydroxyphenyl substituent.

22. The photographic assemblage of claim 21 wherein A is ethylene, n is 1 and Dev is a hydroquinone.

23. In an integral photographic assemblage comprising:
(a) a photosensitive element comprising an opaque support having thereon the following layers in sequence: a red-sensitive silver halide emulsion layer having a diffusible cyan dye developer associated therewith, a green-sensitive silver halide emulsion layer having a diffusible magenta dye developer associated therewith, and a blue-sensitive silver halide emulsion layer having a diffusible yellow dye developer associated therewith;
(b) a transparent sheet superposed over said blue-sensitive silver halide emulsion layer and comprising a transparent support having thereon, in sequence, a neutralizing layer, a timing layer and a dye image-receiving layer; and
(c) a rupturable container containing an alkaline processing composition and an opacifying agent which is so positioned during processing of said assemblage that a compressive force applied to said container will effect a discharge of the container's contents between said transparent sheet and said blue-sensitive silver halide emulsion layer; said assemblage containing a silver halide developing agent; the improvement wherein one of said dye developers has the following formula:

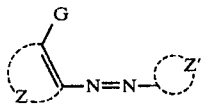

wherein:
Z represents the atoms necessary to complete a phenyl group;
Z' represents a pyrazolotriazole nucleus;
G is a metal chelating group, a salt thereof or a hydrolyzable precursor thereof; said compound also containing a silver halide developing moiety which is capable of developing an exposed silver halide emulsion under photographic processing conditions, and wherein said dye image-receiving layer or a layer adjacent thereto contains metal ions.

24. A process for producing photographic transfer image in color in an imagewise-exposed photographic element comprising a support having thereon at least one photosensitive silver halide emulsion layer having associated therewith a diffusible dye developer compound having the following formula:

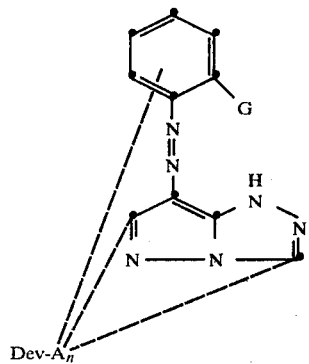

wherein:
Z represents the atoms necessary to complete a phenyl group;
Z' represents a pyrazolotriazole nucleus;
G is a metal chelating group, a salt thereof or a hydrolyzable precursor thereof;
said compound also containing a silver halide developing moiety which is capable of developing an exposed silver halide emulsion under photographic processing conditions, said process comprising:
(a) treating said photographic element with an alkaline processing composition in the presence of a silver halide developing agent to effect development of each of the exposed silver halide emulsion layers;
(b) forming an imagewise distribution of diffusible dye developer as a function of said imagewise exposure of each of said silver halide emulsion layers;
(c) at least a portion of said imagewise distribution of said dye developer diffusing to a dye image-receiving layer; and
(d) contacting said imagewise distribution of said dye developer with metal ions, thereby forming a metal-complexed, dye developer transfer image.

25. The process of claim 24 wherein said dye developer compound has a 7-arylazo-pyrazolotriazole dye moiety, said compound containing said G moiety in the ortho position of the arylazo moiety.

26. The process of claim 25 wherein said compound has the formula:

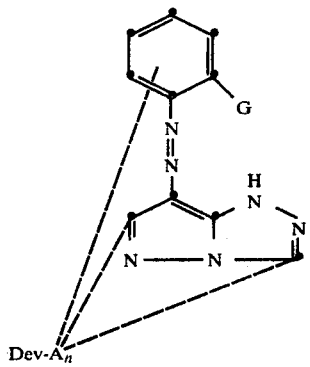

wherein:
G is a metal chelating group, a salt thereof or a hydrolyzable precursor thereof;
A is an organic divalent linking radical;
n is either 0 or 1; and
Dev is said silver halide developing moiety which is a dihydroxyphenyl substituent.

* * * * *